United States Patent
Lambrecht et al.

(10) Patent No.: US 6,821,276 B2
(45) Date of Patent: Nov. 23, 2004

(54) INTERVERTEBRAL DIAGNOSTIC AND MANIPULATION DEVICE

(75) Inventors: Gregory H. Lambrecht, Natick, MA (US); Robert Kevin Moore, Natick, MA (US); Thomas Banks, Santa Barbara, CA (US); Russel J. Redmond, Goleta, CA (US); Claude A. Vidal, Santa Barbara, CA (US); Jacob Einhorn, Brookline, MA (US)

(73) Assignee: Intrinsic Therapeutics, Inc., Woburn, MA (US)

(*) Notice: Subject to any disclaimer, the term of this patent is extended or adjusted under 35 U.S.C. 154(b) by 193 days.

(21) Appl. No.: 10/020,507

(22) Filed: Dec. 11, 2001

(65) Prior Publication Data

US 2002/0156530 A1 Oct. 24, 2002

Related U.S. Application Data

(63) Continuation-in-part of application No. 09/642,450, filed on Aug. 18, 2000, now Pat. No. 6,482,235.
(60) Provisional application No. 60/298,605, filed on Jun. 14, 2001.

(51) Int. Cl.[7] .............................................. A61B 18/18
(52) U.S. Cl. .................................... 606/45; 604/165.01
(58) Field of Search .............................. 606/79, 80, 84, 606/61, 170, 191, 180, 166–167, 41, 45; 604/164.01, 164.13, 165.01, 165.04

(56) References Cited

U.S. PATENT DOCUMENTS

| 5,171,280 | A | | 12/1992 | Baumgartner |
| 5,192,326 | A | | 3/1993 | Bao et al. |
| 5,201,729 | A | | 4/1993 | Hertzmann et al. |
| 5,207,649 | A | * | 5/1993 | Aruny .................. 604/167.01 |
| 5,239,982 | A | | 8/1993 | Trauthen |
| 5,645,597 | A | | 7/1997 | Krapiva |
| 5,743,917 | A | | 4/1998 | Saxon |
| 5,755,797 | A | | 5/1998 | Baumgartner |
| 5,785,705 | A | | 7/1998 | Baker |
| 5,888,220 | A | | 3/1999 | Felt et al. |
| 5,980,504 | A | * | 11/1999 | Sharkey et al. ............. 604/510 |
| 6,019,793 | A | | 2/2000 | Perren et al. |
| 6,102,930 | A | | 8/2000 | Simmons, Jr. |
| 6,120,539 | A | | 9/2000 | Eldridge et al. |
| 6,126,682 | A | | 10/2000 | Sharkey et al. |
| 6,179,836 | B1 | * | 1/2001 | Eggers et al. .................. 606/45 |
| 6,190,353 | B1 | * | 2/2001 | Makower et al. ......... 604/95.01 |
| 6,245,107 | B1 | | 6/2001 | Ferree |
| 6,280,475 | B1 | | 8/2001 | Bao et al. |
| 6,371,990 | B1 | | 4/2002 | Ferree |
| 6,402,750 | B1 | | 6/2002 | Atkinson et al. |
| 6,419,704 | B1 | | 7/2002 | Ferree |
| 6,428,576 | B1 | | 8/2002 | Haldimann |
| 6,491,690 | B1 | * | 12/2002 | Goble et al. .................. 606/41 |
| 6,520,967 | B1 | | 2/2003 | Cauthen |
| 6,579,291 | B1 | | 6/2003 | Keith et al. |
| 2002/0007218 | A1 | | 1/2002 | Cauthen |
| 2002/0077701 | A1 | | 6/2002 | Kuslich |
| 2002/0111688 | A1 | | 8/2002 | Cauthen |

(List continued on next page.)

FOREIGN PATENT DOCUMENTS

| WO | WO 00-044288 | | 8/2000 |
| WO | WO0128468 | A1 | 4/2001 |
| WO | WO 02-058599 | | 8/2002 |
| WO | WO 02-067824 | | 9/2002 |

*Primary Examiner*—Julian W. Woo
*Assistant Examiner*—Victor Nguyen
(74) *Attorney, Agent, or Firm*—Knobbe, Martens, Olson & Bear, LLP; Sean Kavanaugh, Esq.

(57) ABSTRACT

The present invention relates generally to intervertebral disc devices and methods and instrumentation for intervertebral disc procedures. An intervertebral disc repair and diagnostic device that is minimally invasive, actively guided, and provides direct and consistent access to the inner surface of the posterior anulus, which will not unintentionally exit the posterior anulus and cause harm to the spinal cord, is provided.

14 Claims, 12 Drawing Sheets

U.S. PATENT DOCUMENTS

| | | |
|---|---|---|
| 2002/0120337 A1 | 8/2002 | Cauthen |
| 2002/0123807 A1 | 9/2002 | Cauthen, III |
| 2002/0147496 A1 | 10/2002 | Belef et al. |
| 2002/0151980 A1 | 10/2002 | Cauthen |
| 2002/0165542 A1 | 11/2002 | Ferree |
| 2002/0189622 A1 | 12/2002 | Cauthen, III et al. |
| 2002/0198599 A1 | 12/2002 | Haldimann |
| 2003/0004574 A1 | 1/2003 | Ferree |
| 2003/0040796 A1 | 2/2003 | Ferree |
| 2003/0074075 A1 | 4/2003 | Thomas, Jr. et al. |
| 2003/0074076 A1 | 4/2003 | Ferree et al. |
| 2003/0078579 A1 | 4/2003 | Ferree |

* cited by examiner

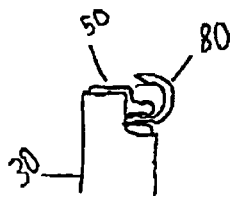
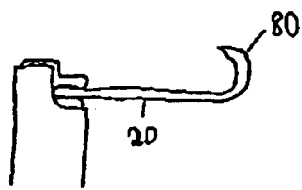
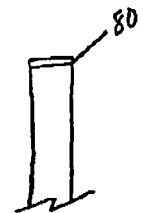
Figure 11a     Figure 11b     Figure 12
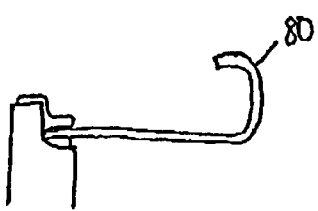
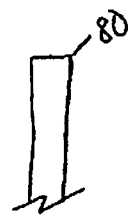
Figure 13a     Figure 13b     Figure 14
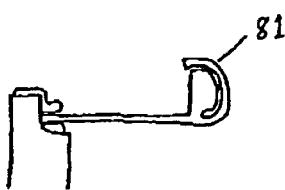
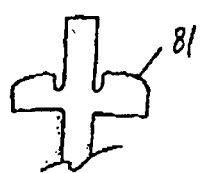
Figure 15a     Figure 15b     Figure 16

INTERVERTEBRAL DIAGNOSTIC AND MANIPULATION DEVICE

RELATED APPLICATIONS

This application is a continuation in part of U.S. application Ser. No. 09/642,450 filed Aug. 18, 2000 now U.S. Pat. No. 6,482,235 and claims priority under 35 U.S.C. §119(e) to U.S. Provisional Application No. 60/298,605 filed on Jun. 14, 2001.

BACKGROUND OF THE INVENTION

1. Field of the Invention

The present invention relates generally to devices and instrumentation for intervertebral disc diagnosis and treatment, and methods thereof.

2. Description of the Related Art

An intervertebral disc performs the important role of absorbing mechanical loads while allowing for constrained flexibility of the spine. The disc is composed of a soft, central nucleus pulposus surrounded by a tough, woven anulus fibrosis. Herniation is a result of a weakening in the anulus. Symptomatic herniations occur when weakness in the anulus allows the nucleus to bulge or leak posteriorly toward the spinal cord and major nerve roots. The most common symptoms of herniation include pain radiating along a compressed nerve and lower back pain, both of which can be crippling for the patient. Herniation, and the resulting dehabilitating symptoms, are of significant medical concern in the United States because of the low average age of diagnosis. Indeed, over 80% of patients in the United States diagnosed with herniation are under the age of 59.

Information regarding anular thickness, internal dimensions of the disc space normally occupied by the nucleus, and the location of anular apertures and lesions in relation to the vertebral endplates and lateral walls of the anulus facilitates accurate diagnosis and treatment of intervertebral disc conditions. For example, medical procedures involving the implantation of an artificial nucleus or anular augmentation depend on this information for accurate sizing of such implants. Also important are safe, dependable, and minimally invasive methods and devices for the manipulation of anular and nuclear tissue, especially along the inner wall of the posterior anulus. For example, tissues in the anulus and nucleus are commonly removed or manipulated during the implantation of artificial discs either to clear a path for the insertion of other types of prosthetic devices or as part of a discectomy procedure.

Specialized tools have evolved for the surgical treatment of intervertebral discs in the lumbar, cervical, and thoracic spine, which have suffered from tears in the anulus fibrosis or herniation of the nucleus pulposus. These tools are well-known in the prior art. The devices of the prior art, however, are designed for specific procedures, including complete discectomies (as opposed to partial discectomy or minute removal of tissue) and the installation of vertebral fusion implants. Accordingly, these devices cannot be used to manipulate anular and nuclear tissue in a precise and minimally invasive manner. Moreover, such devices are typically designed to access the disc using an anterior approach, i.e., through the abdomen. Although an anterior surgical approach provides direct access to intervertebral discs, it is highly invasive to the abdominal organs. Thus, surgery is typically more complicated and time consuming. A direct posterior approach is not anatomically practicable because the spinal cord and its surrounding bony protective sheath lies directly in front of each vertebral disc. An posterior-lateral aspect approach is the least invasive of these methods but provides limited and oblique access to the disc and its interior. Depending upon the surgical necessities involved, several methods of percutaneous disc tissue manipulation are available, including chemonucleolysis (e.g., U.S. Pat. No. 4,439,423), laser (e.g., U.S. Pat. No. 5,437,661), manual, focused energy, ultrasonic disruption (e.g., U.S. Pat. No. 5,772,661), arthroscopy and endoscopy.

Endoscopic instrumentation has evolved over the past 25 years and permits viewing, irrigation, suction, and cutting. Probes that permit automated percutaneous suction such as nucleotomes or cylindrically housed rotating cutting means, such as debreders, provide gross but efficient removal of disc tissue. Varying tip profiles control the amount and direction of tissue resection as well as the likelihood of damage to surrounding tissue. These devices tend to be limited by the size of the cannula which houses the instrumentation and its ability to maneuver around vertebral bodies and delicate tissues of the spine.

Hand tools for use in the spine are also well known and can be inserted through cannulae or freely guided by hand. These tips may be blades, burs, rongeurs, curettes or forcep-like "graspers" that are capable of pinching of small amounts of material. To the extent that these instruments can access the various tissues, these devices provide good tactical feedback and control. However, if used in an antero-lateral spinal approach, these tools are generally limited by the indirect approach necessitated by the laminae and spinous processes of the adjacent vertebrae, and thus, access to tissues is substantially hampered.

Some intervertebral disc devices have been designed with flexible tips that are designed not to perforate or deflect off of the interior surface of the disc. Unfortunately, such tips deflect off of healthy disc tissue only, not the pathological tissue that caused the need for the surgery in the first place. Thus, such instrumentation can exit the anulus and cause considerable damage to the surrounding tissues and spinal cord. Also, the flexible probe tips on some instruments which permit access to remote locations within the disc can only do so by sacrificing direct control because the devices are passively guided or blindly "snaked" within the disc. Accordingly, delicate and precise work within a disc is not possible with such instruments.

Among other disadvantages, the devices and methods of the prior art are typically invasive and destructive to surrounding tissue, frequently causing disc infection and nerve root injury. Moreover, such devices are unable to precisely manipulate disc material along the posterior anulus in a minimally invasive manner. Accordingly, there is a need for an intervertebral disc diagnostic and manipulation device which is capable of performing delicate and precise work within a disc, especially along the posterior anulus and between anular lamella.

SUMMARY OF THE INVENTION

The current invention relates generally to devices and instrumentation for intervertebral disc diagnosis and treatment, and methods thereof. In several embodiments, the present invention provides for a minimally invasive and actively guided intervertebral disc repair and diagnostic device. This device provides direct and consistent access to the inner surface of the posterior anulus and will not unintentionally exit the posterior anulus and cause harm to the spinal cord. One skilled in the art will understand that this device is not limited to intervertebral disc applications, but includes medical procedures in which a minimally invasive, actively guided device for diagnosis, repair or treatment is desired. These procedures include, but are not limited to, arthroscopic, endoscopic, and endovascular applications. Further, one skilled in the art will appreciate that, in many embodiments, this invention may be used percutaneously or intralumenally.

Various embodiments of the invention may be guided by tactile feedback or through active viewing. Also, various embodiments may be used in conjunction with medical imaging technologies, including MRI, ultrasound, or fluoroscopy. Further, several embodiments of the invention having radiopacity or selective radiopacity may be used in conjunction with imaging methods for guidance and/or to facilitate measurement of organs or tissues.

Various embodiments of the current invention are particularly advantageous because they provide active controlled direction of the working end of the instrument within the anulus or nucleus. Further, several embodiments provide access to the posterior portion of the anulus using a posterior surgical approach. In various embodiments, access to the posterior anulus, via circumferential navigation of the instrument as it is deflected from the lateral, anterior, opposite lateral, and finally to the posterior anulus, is avoided. This is advantageous because circumferential deflection of the working end of the instrument within the anulus can result in the tip of the instrument passing through a fissure in the posterior anular surface and outward to the spinal cord. This can occur because the circumferential navigation from a typical posterior surgical approach eventually directs the tip perpendicular to the posterior anular surface, which may contain lesions large enough to allow protrusion of the tip directly through to the spinal cord.

There is provided in accordance with one aspect of the present invention, a device for treating the spine. The device comprises an elongate guide having a longitudinal axis. An axially moveable actuator is carried by the guide. A probe is movable with the actuator, and a deflection surface is carried by the guide. Axial movement of the actuator causes the probe to advance along the deflection surface and extend away from the guide at an angle to the longitudinal access of the guide.

In one implementation of the invention, the guide comprises an elongate tubular body having at least one lumen extending therethrough. The actuator extends through at least a portion of the guide. The probe may comprise an elongate flexible body, attached to the actuator. The probe may be biased in a nonlinear configuration. In one embodiment, the probe comprises a nickel titanium alloy.

In accordance with another aspect of the present invention, there is provided a method of treating a disc in the spine. The method comprises the steps of advancing a device at least part way through an anulus. A probe is advanced laterally from the device in a first direction along a portion of the anulus.

In one application of the invention, the advancing a probe step comprises advancing the probe in between adjacent (anular lamella) layers of the anulus. In another application of the invention, the advancing a probe step comprises advancing the probe along an interior surface of the anulus, between the anulus and the nucleus. The method may further comprise the step of repositioning the probe and advancing the probe in a second direction along a second portion of the anulus.

In accordance with a further aspect of the present invention, the method additionally comprises the step of introducing media through the delivery device and into the disc. In one application, the media comprises contrast media, to permit fluoroscopic visualization. The media may alternatively or additionally comprise a medication, and/or a nucleus augmentation material. The method may additionally comprise the step of introducing a prosthesis into the disc. The prosthesis may be introduced by proximately retracting a push rod from a lumen in the delivery device, and introducing the prosthesis into the disc through the lumen.

As will be appreciated by those of skill in the art, the present invention, therefore, provides a minimally invasive access pathway into the anulus and/or nucleus of a vertebral disc. The pathway may be utilized to perform any of a wide variety of procedures, including diagnostic and therapeutic procedures, some of which will be identified below.

Several embodiments of this invention provide a new intervertebral disc manipulation and diagnostic device.

One or more embodiments disclosed herein provide a convenient, reliable, and accurate way to measure the anular thickness and the internal dimensions of the disc space normally occupied by the nucleus pulposus.

Several embodiments of this invention provide a device useful in determining various disc dimensions in order to enable a surgeon to size various implants and tools and facilitate their guidance within the disc.

Various embodiments provide for the manipulation through an opening in the anulus. Manipulation includes, but is not limited to, dissection, resection or ablation of disc tissue. The opening may be a single iatrogenic hole, such as an anulotomy, a naturally occurring hole, or a lesion in the anulus.

One or more aspects of the current invention prepare or manipulate disc tissue in preparation for the insertion of an implant or other instruments.

Several embodiments of the present invention diagnose and manipulate disc tissue with minimal invasiveness and risk of unintended passage of the device outside of the posterior anulus in the direction of the spinal cord or other sensitive areas proximal thereto.

Various aspects of this invention permit direct access to the interior aspect of anulus via an anulotomy.

Several embodiments of invention provide an intervertebral disc manipulation and diagnostic device wherein the travel of the working end of the device is parallel to the lamellae of the anulus.

This disclosure utilizes particular orthopedic references, nomenclature, and conventions. Accordingly, several background figures and descriptions are included to aid in the understanding of the environment under which specific embodiments of the invention may be used. In this description and the following claims, the terms "anterior" and "posterior", "superior" and "inferior" are defined by their standard usage in anatomy, i.e., anterior is a direction toward the front (ventral) side of the body or organ, posterior is a direction toward the back (dorsal) side of the body or organ; superior is upward (toward the head) and inferior is lower (toward the feet).

BRIEF DESCRIPTION OF THE DRAWINGS

FIG. 1A is a view of a transverse section. FIG. 1B is a view of a sagittal section.

FIG. 11A is a side view of the intradiscal tip of the device showing a variation of the probe tip. In this variation, the trailing edge of the reverse-curved tip has been sharpened. In FIG. 11B, the same intradiscal tip is shown with the probe advanced from its initial retracted position.

FIG. 12 is a top view of the probe from FIGS. 11A and 11B shown unformed. The probe is shown as it would appear prior to forming, if it were formed from a flat sheet of material, sharpened along one edge.

FIG. 13A is a side view of the intradiscal tip of the device, showing a variation of the probe tip. In this variation, the distal end of the reverse-curved tip is spaced further distally from the distal end of the device than that of the probe depicted in FIGS. 11a–b. In FIG. 13B the same device is shown with the probe advanced from its initial retracted position.

FIG. 14 is a top view of the probe from FIGS. 13A and 13B shown unformed. The reverse curve that forms the distal tip of the probe is shown as it would appear prior to forming, if it were formed from a flat sheet of material.

FIG. 15A is a side view of a variation of the probe tip. In this variation, the tip of the reverse curve has two additional flanges of material on either side of the curve. The combination of tip elements forms a scoop. In FIG. 15B the same device is shown with the probe advanced from its initial retracted position.

FIG. 16 is a top plan view of the probe from FIGS. 15A and 15B shown unformed. The two side flanges and the reverse curve that forms the distal tip of the probe are shown as they would appear prior to forming, if they were formed from a flat sheet of material.

DETAILED DESCRIPTION OF THE PREFERRED EMBODIMENT

Figure 1A:
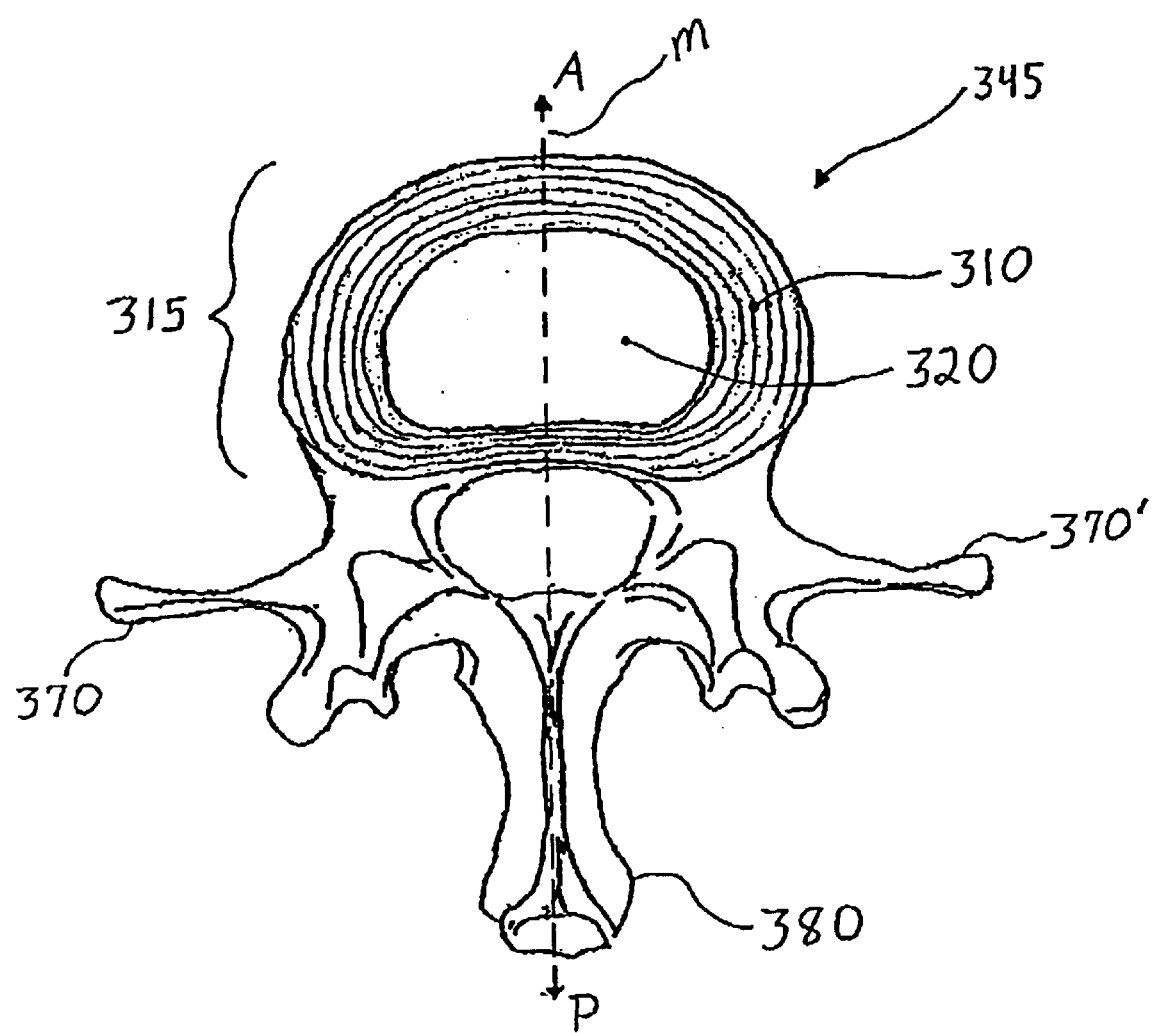
FIGS. 1A and 1B show the general anatomy of a functional spinal unit 345.

In one aspect of the invention, there is provided a guide such as a hollow delivery cannula having a distal end and a proximal end. The guide is dimensioned to fit within a small anulotomy as might be created by a surgeon or through a naturally occurring hole or lesion in the anulus. An advancer, push rod, or actuator is axially moveably carried by the guide, and coupled to a flexible probe member. The flexible probe member has a proximal end connected to the advancer and distal end connected to or formed into a probe tip.

The probe is advanceable outwardly from the distal end of the cannula via axial movement of the advancer within the cannula. In the illustrated embodiment, the probe member exits through a slot having a curved pathway or deflection surface located at the distal end of the cannula and can be advanced outwardly therefrom generally at an angle of between about 30 to about 150 degrees relative to the cannula's longitudinal axis. Accordingly, when the distal end of the cannula is properly inserted within the anulotomy at sufficient depth, the probe travels along a path that is parallel to and along the surface of or in between the anular lamellae. The probe may be retracted via reversing the action (e.g. proximal retraction) of the advancer.

A means for measuring the distance advanced by the probe is associated with the probe and cannula. Any of a variety of measurement indicia may be used, such as calibrated markings on the advancer visible through or proximal to the cannula. An indicator for measuring the distance advanced by the cannula within the anulotomy or lesion may also be included. For example, a calibrated depth stop may be affixed in a slideably adjustable manner to the delivery cannula.

The probe tip at the distal end of the probe member may be an integral piece of the probe wherein the tip and the probe are of a unitary construction. Alternatively, the tip may be secured, either releasably or permanently to the probe. The tip can be blunt enabling it to forcibly part the tissue without cutting it (blunt dissection) or be sharpened to present a sharp dissecting blade surface (sharp dissection).

The tip may also be constructed in a backwardly curved manner facing back towards the longitudinal axis of the cannula and with its reverse facing edge sharpened to facilitate resection or sharp dissection as it is retracted. This curved shape also serves to present a blunt profile that is less likely to perforate the anulus as it is advanced, even in the presence of uneven or degenerated anular tissue. Alternatively, the curved resection tip or blade may be formed as a multi-sided scoop with a concave trailing surface and convex leading surface such that it presents a blunt frontal profile even when advanced off-angle into the anulus or toward a vertebral endplate.

In another embodiment, the tip may be configured to house an ablation element. This element may be preferentially insulated on particular surfaces of the probe and/or tip to minimize unwanted damage to adjacent tissues. For example, the surface of the probe or tip facing an inner aspect of the anulus may be insulated to prevent unwanted travel through or harm other portions of the anulus, nucleus and vertebral endplates. Ablation energy is instead directed to the targeted tissue adjacent to the probe tip and not the endplates or tissue facing the insulted side of the probe tip.

FIG. 1A is an axial view along the transverse axis M of a vertebral body with the intervertebral disc 315 superior to the vertebral body. Axis M shows the anterior (A) and posterior (P) orientation of the functional spine unit within the anatomy. The intervertebral disc 315 contains the anulus fibrosus (AF) 310 which surrounds a central nucleus pulposus (NP) 320. Also shown in this figure are the left 370 and right 370' transverse spinous processes and the posterior spinous process 380.

Figure 1B:
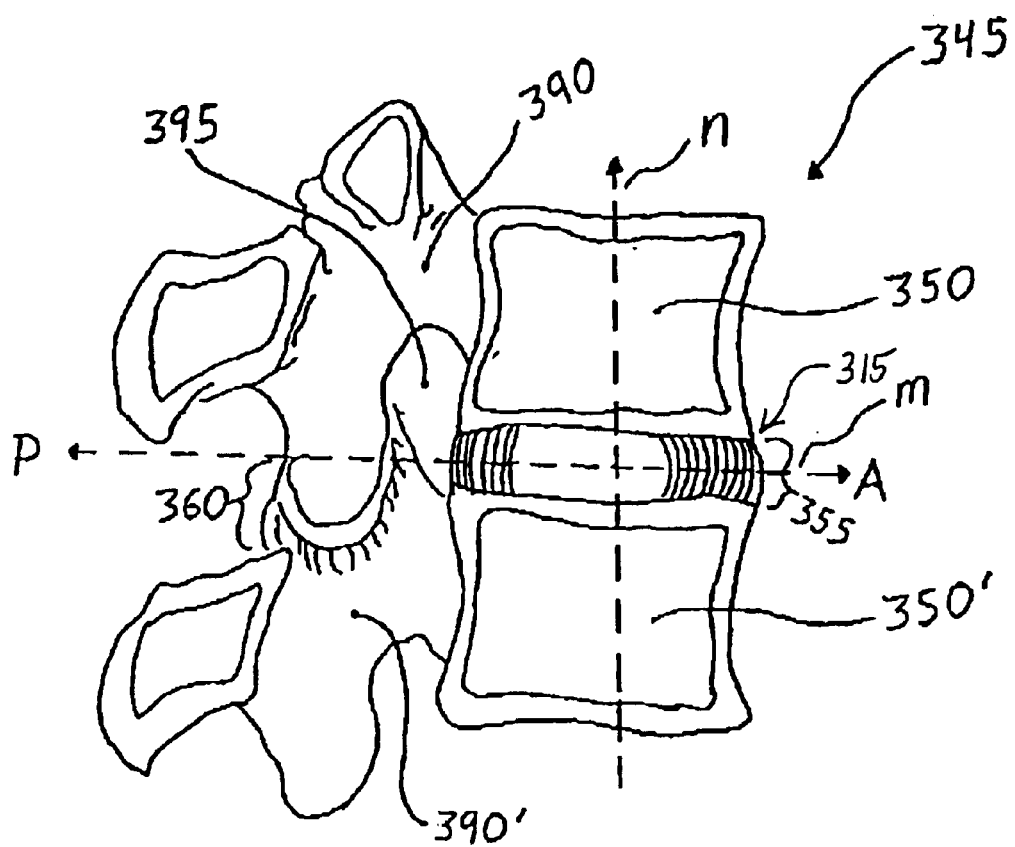
Figure 1C:
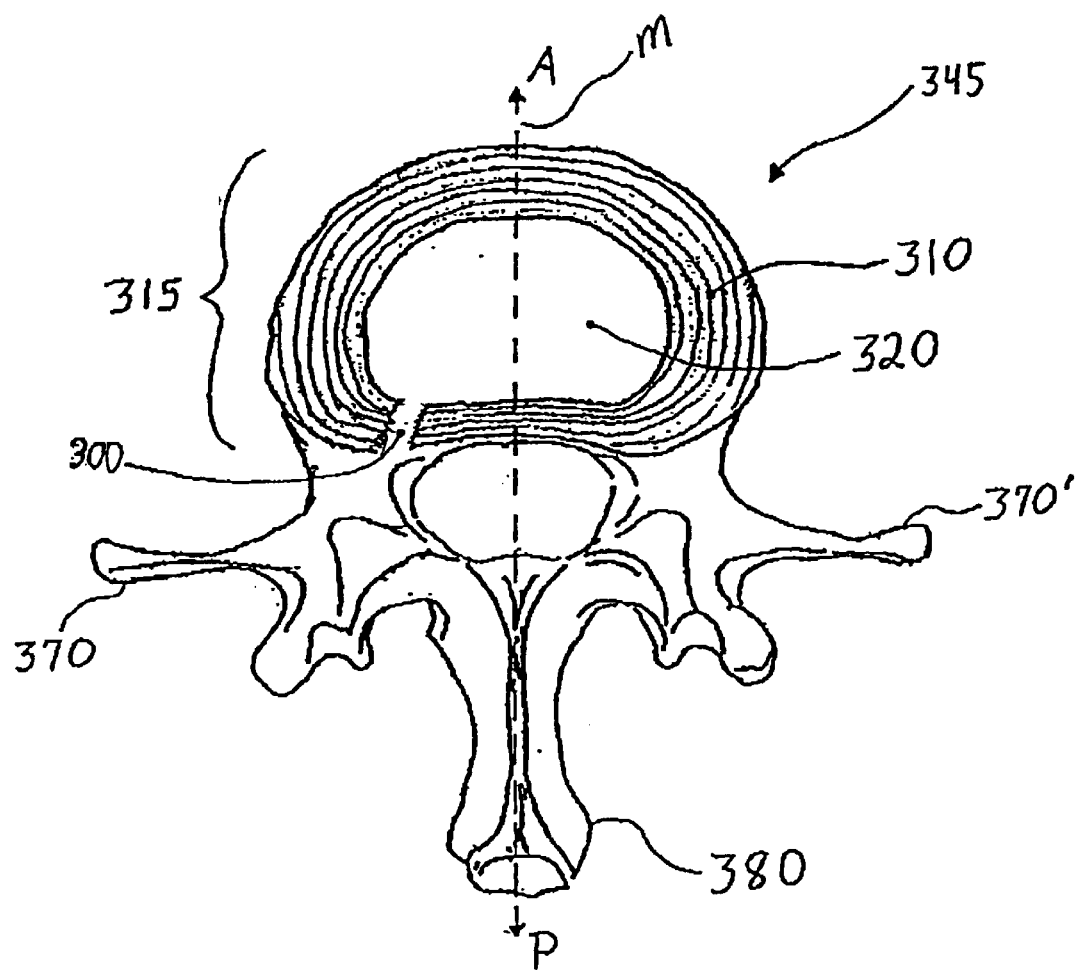
FIG. 1C shows the same functional spine unit with a defect in the anulus, which may have been created iatrogenically, as in the performance of an anulotomy, or may be naturally occurring.

FIG. 1B is a sagittal section along sagittal axis N through the midline of two adjacent vertebral bodies 350 (superior) and 350' (inferior). Intervertebral disc space 355 is formed between the two vertebral bodies and contains intervertebral disc 315, which supports and cushions the vertebral bodies and permits movement of the two vertebral bodies with respect to each other and other adjacent functional spine units.

Intervertebral disc 315 is comprised of the outer AF 310 which normally surrounds and constrains the NP 320 to be wholly within the borders of the intervertebral disc space. Axis M extends between the anterior (A) and posterior (P) of the functional spine unit. The vertebrae also include facet joints 360 and the superior 390 and inferior 390' pedicle that form the neural foramen 395.

Figure 2A:
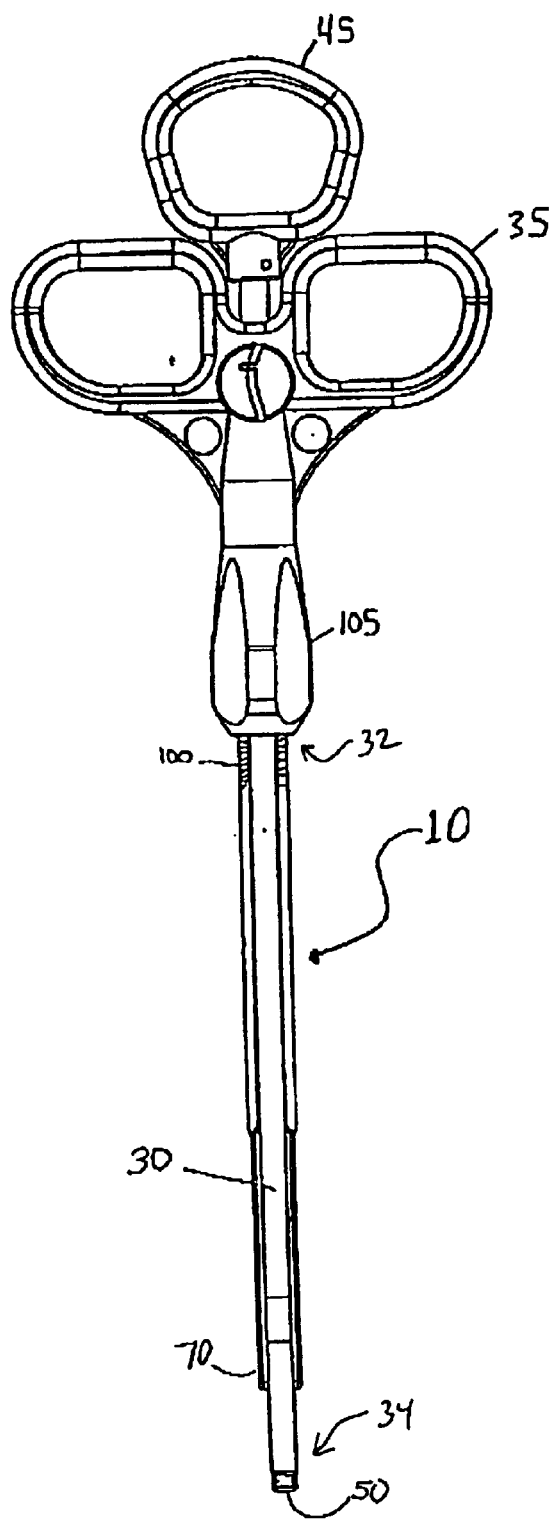
FIGS. 2A and 2B are front and side views of a device in accordance with the present invention.
Figure 2B:
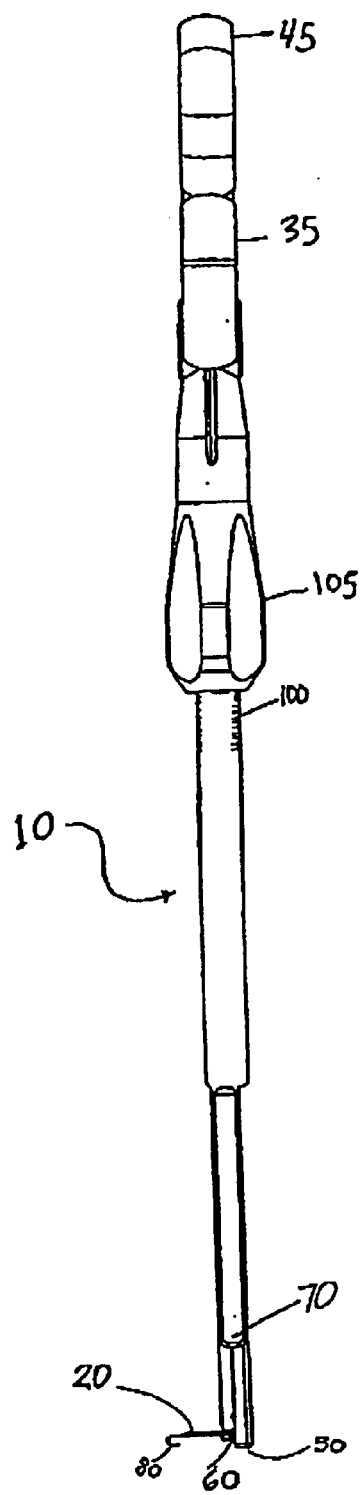
Figure 3:
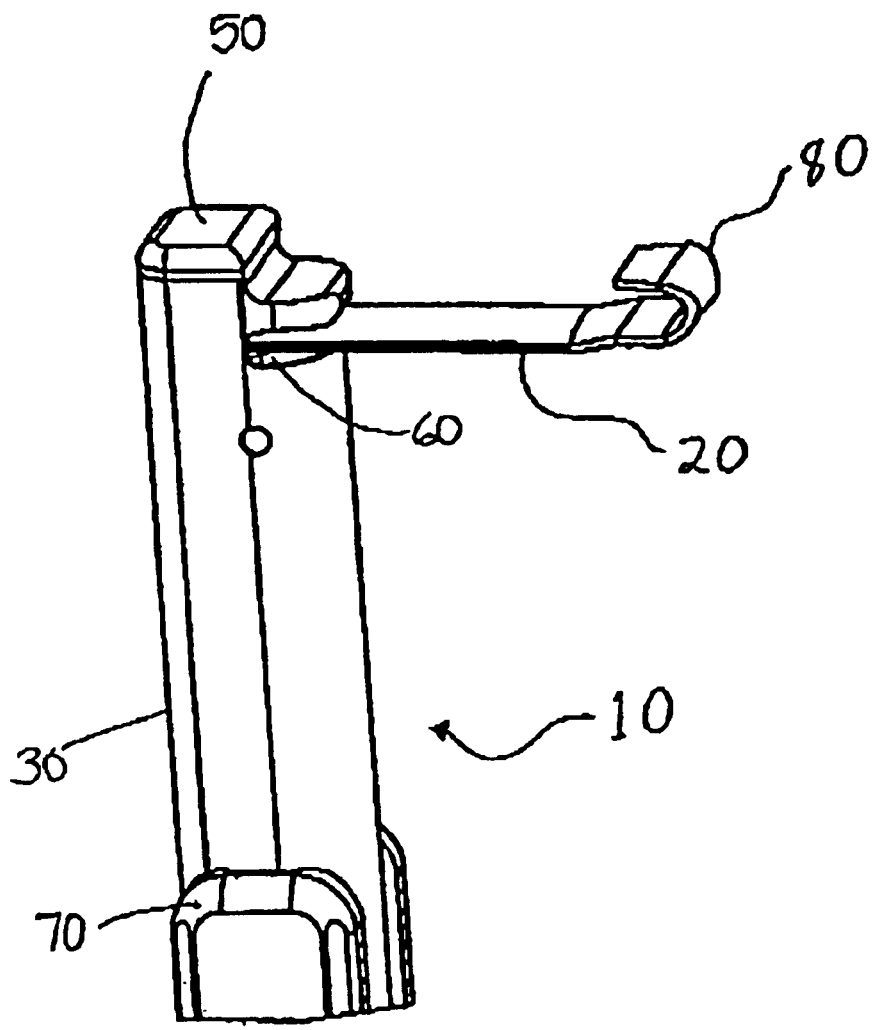
FIG. 3 is an isometric view of the distal end of the device.

Referring FIG. 2a, the device 10, a cannula handle 35, and a ring handle 45 are positioned such that the device 10 may be operated by one hand, i.e. utilizing the thumb, index, and ring fingers to position the device 10 and advance and retract the probe member 20. However, any of a variety of proximal handpieces can alternatively be used, including triggers, slider switches, rotatable knobs or other actuators to advance and retract the probe 20 as will be apparent to those of ordinary skill in the art in view of the disclosure herein.

Figures 4, 5, 6:
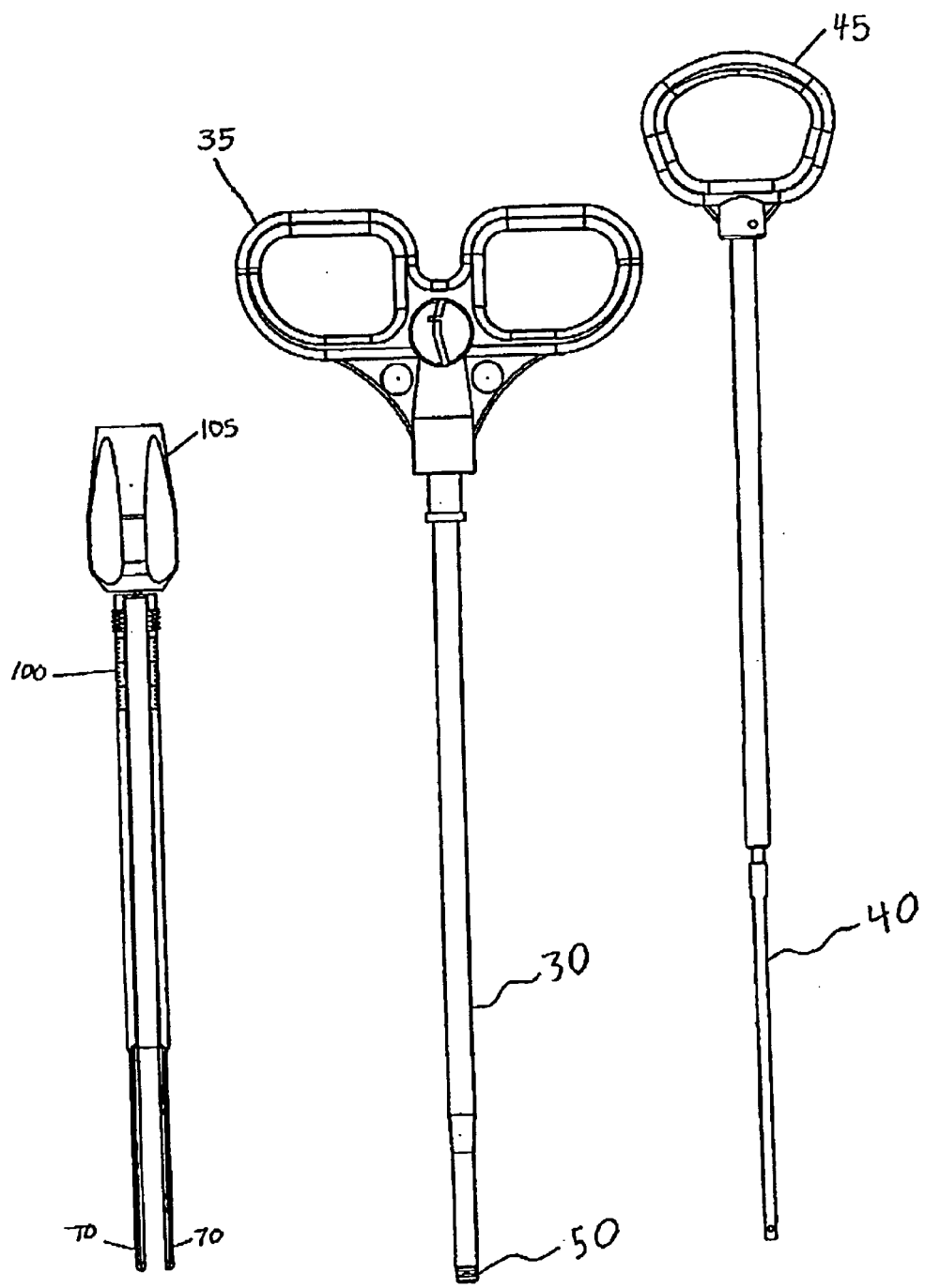
FIG. 4 is a side view of the depth stop components of the device including depth-measuring markings, the depth stop adjustment knob, and the depth stop body.
FIG. 5 is a side view of the delivery cannula, cannula handle and intradiscal tip.
FIG. 6 is a side view of the advancer, with a ring-handle.

In FIG. 5 the cannula handle 35 is secured to the proximal end 32 of an outer delivery cannula 30. Outer delivery cannula 30 extends from the proximal end 32 to a distal end 34 which is provided with an intradiscal tip 50. Delivery cannula 30 functions as a guide for the axial reciprocal movement of a push rod 40 as will be discussed. Delivery cannula 30 may, therefore, be provided in the form of an elongate tube having a central lumen for receiving push rod 40 therethrough. Alternatively, the guide may comprise a nontubular structure, in an embodiment in which the push rod travels concentrically over or alongside the guide.

The delivery cannula 30 may be manufactured in accordance with any of a variety of techniques well known in the medical device arts. In one embodiment, the cannula 30 comprises a metal tube such as stainless steel or other medical grade metal. Alternatively, the cannula 30 may comprise a polymeric extrusion such as high density polyethylene, PTFE, PEEK, PEBAX, or others well known in the medical device arts.

In general, the axial length of the delivery cannula 30 will be sufficient to reach the desired treatment site from a percutaneous or small incision access through the skin. Lengths within the range from about 10 centimeters to about 30 centimeters are contemplated, with a length from a proximal end 32 to distal end 34 within the range of from about 14 to about 20 centimeters contemplated for most posterior lateral access pathways. The length may be varied depending upon the intended access pathway and patient size.

Preferably, the outside diameter of the delivery cannula 30 is no greater than necessary to accomplish the intended functions disclosed herein. In general, outside diameters of less than one centimeter are preferred. In typical embodiments of the present invention, the delivery cannula 30 has an outside diameter of no greater than approximately 5 millimeters.

Referring to FIG. 6, the push rod or advancer 40 comprises an elongate body 42 having a proximal end 44 and a distal end 46. Push rod 40 may comprise a solid rod or tubular component as may be desired, depending upon the construction materials and desired physical integrity. In one embodiment, the push rod 40 comprises a solid metal rod, such as stainless steel or other suitable material. Alternatively, a polymeric extrusion using any of a variety of known medical grade polymers may be used.

Push rod 40 is preferably dimensioned to extend throughout the length of the delivery cannula 30, so that the probe 20 is fully extended from the intradiscal tip 50 when the ring handle 45 is brought into contact with the cannula handle 35 or other stop surface.

The device 10 may optionally be provided with one or more axially extending lumens, for placing the proximal end of the device 10 in fluid communication with the distal end, for any of a variety of purposes. For example, one or more lumens may extend through the push rod 40. Alternatively or in addition, the outside diameter of push rod 40 may be dimensioned smaller than the inside diameter of the delivery cannula 30 to create an annular space as is well understood in the catheter arts. A first lumen may be utilized for introduction of radiopaque dye to facilitate visualization of the progress of the probe 20 and or distal end of the device 10 during the procedure. The first lumen or second lumen may be utilized to introduce any of a variety of media such as saline solution, or carriers including any of a variety of medications such as anti-inflammatory agents e.g,. steroids, growth factors e.g., TNfα antagonists, antibiotics, and functional proteins and enzymes e.g., chympopapain. A lumen may also be utilized to aspirate material such as nucleus pulposus, and/or to introduce nucleus augmentation material during or at the end of the procedure.

Figure 7:
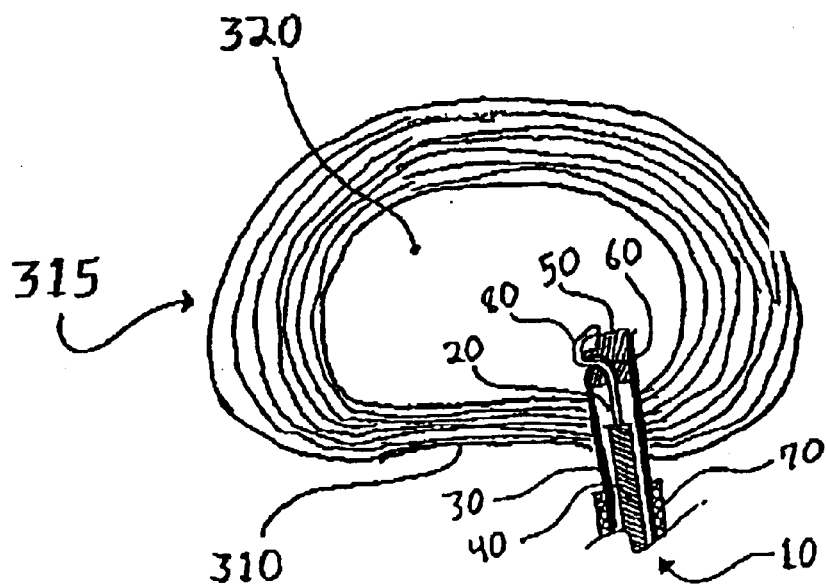
FIG. 7 is a cross-sectional view of the device with the intradiscal tip positioned within an anulotomy. The probe and depth stop are both retracted, and the distal end of the device has been inserted to a depth beyond the anterior aspect of the posterior anulus.

Referring to FIG. 7, the distal end 34 of device 10 is shown in cross section. Distal end 34 includes an axially moveable probe member 20, an outer delivery cannula 30 and an advancer or inner push rod 40. A curved passage or slot 60 is proximal an intradiscal tip 50 of the delivery cannula 30. The passage or slot 60 includes a curved distal deflection surface which acts to deflect the probe member 20 in a path that is roughly parallel to the lamellae of the posterior anulus fibrosus 310 as the probe member 20 is advanced outwardly from the curved slot 60 and into the disc 315 by the advancer 40.

The distal end 34 of the cannula 30 may be provided with any of a variety of constructions, depending upon the mode of deflection of the probe 20. In the illustrated embodiment, the distal end 34 is provided with a cap 52 which contains the deflection surface 62 therein. Cap 52 may be molded from any of the polymeric materials identified elsewhere herein, and secured to the distal end 34 by adhesive bonding, interference fit, or other conventional securing technique. Cap 52 has an atraumatic distal surface 50, which may comprise the distal end of cap 52, or may include a coating or layer of an atraumatic material such as silicone, carried by the cap 52.

Any of a variety of alternative deflection surfaces may be used, depending upon the desired distal tip design. For example, the distal molded cap 52 may be eliminated, and the deflection surface formed instead by an inside surface of the tubular cannula 30. This may be accomplished by providing two opposing axial slots extending proximally from the distal end 34 of the cannula 30 to isolate two opposing axial ribbons on the distal end 34. A first one of the ribbons is severed and removed, while the second one is curved across the central axis of the cannula 30 to provide a curved deflection surface.

Alternatively, the deflection surface may be eliminated in certain circumstances. For example, in the procedure illustrated in FIG. 7, the device is inserted through a defect in the posterior annulus at an angle relative to the desired treatment plane that requires the probe 20 to exit the device at a corresponding angle in order to advance the probe along the surface of or within the annulus as shown (e.g., within or parallel to the desired treatment plane). However, by moving the access path through the annulus roughly 80–90 degrees counterclockwise as viewed in FIG. 7, the longitudinal axis of the device 10 can be positioned coplanar or parallel to the posterior interior surface of the annulus or other desired treatment plane. In this orientation, the probe is desirably launched axially out of the end of the cannula 30, to dissect a space for subsequent annulus patch implantation.

The foregoing axial launch embodiment of the invention may be utilized through the naturally occurring defect. However, the axial launch device is more likely to find application through an iatrogenic access pathway, created through the annulus spaced apart from the natural defect such that the longitudinal axis of the iatrogenic access is substantially parallel (e.g., no more than about +/−20 degrees) from the plane in which the natural defect resides.

As a further alternative, the probe 20 may be laterally deflectable in response to manipulation of a deflection control at the proximal end of the device 10. For example, the probe 20 in one construction comprises a flexible metal or polymeric ribbon, extending from the distal end of the advancer 40 or other axial support. An axially extending steering element is attached to the probe 20. Generally the steering element will be attached near the distal end of the probe 20. Axial proximal or distal movement of the steering element relative to the advancer 40 will cause a lateral deflection of the probe 20.

The radius of curvature of the deflection can be controlled in a variety of ways as will be apparent to those of skill in the art in view of the disclosure herein, such as by varying the lateral flexibility of the probe 20, and the attachment point of the steering element to the probe 20. Due to the differing physical requirements of devices under tension compared to compression, the cross section of the device may be minimized if the steering element is a pull wire or ribbon such that axial proximal retraction of the pull wire relative to the probe 20 causes a lateral deflection of the probe 20. The lateral deflection can be coordinated with the extent of distal advance to cause the probe to follow the desired curved path either by mechanics in the proximal handpiece, or by the clinician. For this purpose, the proximal handpiece can be provided with any of a variety of controls, such as slider switches or rotatable levers or knobs to allow the clinician to control deflection as well as distal (and lateral) advance.

In an alternate construction, the probe launches axially from the distal end 34 of the cannula or other guide 30, but curves under its own bias to travel in a lateral arc and slide along the posterior annulus or other desired surface. This may be accomplished by constructing the probe from a nickel—titanium alloy such as Nitinol and providing it with a lateral pre bent orientation. The probe is restrained into an axial orientation within the cannula 30, but extends laterally under its own bias as it is advanced distally from an opening in the distal end of the cannula 30.

The probe member 20 in the illustrated embodiment may be formed from a superelastic nickel titanium alloy, or any other material with suitable rigidity and strain characteristics to allow sufficient deflection by deflection surface 62 without significant plastic deformation. The probe member 20 can be formed from an elongated sheet, tube, rod, wire or the like. Probe 20 may also be constructed in various cross-sectional geometry's, including, but not limited to hemicircular, semicircular, hollow, and rectangular shapes.

A probe tip 80 at the distal end of the probe member 20 can be used to dissect between the anulus 310 and nucleus 320, to dissect between layers of the anulus 310, or to dissect through the nucleus. The probe tip 80 can be constructed of the same material as the probe member 20 or another suitable material for the purposes of cutting or presenting a blunt rounded surface. A sharpened surface on the distal edge of the probe member 20 forming the probe tip 80 can be used to dissect a path to enable the insertion of an implant in the created space. Similarly, a blunted tip profile may be used to separate or disrupt anular lamella and create an open space between the anulus 310 and nucleus 320 or within the nucleus 320 itself.

The probe tip 80 may also be provided with a backward curve as shown in FIGS. 11A and 11B. In this construction, a concave surface faces the longitudinal axis of the device when deployed within the disc. The tip 82 may be sharpened to facilitate resection or sharp dissection as it is retracted. This curved shape will also serve to present a blunt profile to reduce the risk of perforating the anulus 310 as it is advanced, even in the presence of uneven or degenerated anular tissue. The curved tip 80 may be formed in any of a variety of radii or shapes depending on the amount of material one desires to remove on each pass of the probe member 20 into the disc, as shown in FIGS. 13A and 13B. Alternatively, the resection tip 80 or blade may be formed as a multi sided concave scoop 81 having a cavity therein such that it presents a blunt convex frontal profile even when advanced off-angle into the anulus 310 or toward a vertebral endplate 350, as shown in FIGS. 15A and 15B. Also, the increased surface area of such a scoop 81 would serve to further facilitate removal of disc tissue.

The distal end of device 10 is shown in FIG. 7 as inserted through a defect in the posterior anulus 300. Alternatively, the device 10 could be inserted through defects in the posterior-lateral, lateral, or anterior anulus 300. In these alternate positions, the probe tip 80 can be advanced parallel to the lamellae of different regions of the anulus 310. One of the many advantages of the curved, distal probe tip 80, as represented in several embodiments of the current invention, is its minimal profile when the probe is in its retracted state relative to the outer cannula 30. In this state, depicted in FIG. 7, the curved tip 80 fits around the distal end of intradiscal tip 50, only minimally increasing the size or profile of device 10. This minimizes the size of the defect in the anulus 300 necessary to allow proper insertion of the distal end of device 10.

As demonstrated in FIGS. 11 and 13, various geometry's of the tip 80 can be employed without increasing the necessary anular defect or anulotomy 300 size for insertion of the intradiscal tip 50 of the device 10. For example, the larger radius of the probe tip 80 in FIG. 13 presents a blunter dissection profile when advanced from the intradiscal tip 50 without necessitating a correspondingly larger anulotomy 300 for proper insertion of the device 10 into the disc. As the bluntness of probe tip 80 is increased, it may be desirable to increase the stiffness of the probe 20. This increased stiffness may be achieved in a variety of ways which can include, but is not limited to using a thicker or more rigid material for forming probe 20, or by using a curved cross-sectional shape along the length of probe 20. These techniques may be used to stiffen all or a portion of the length of probe 20.

Figure 17A:
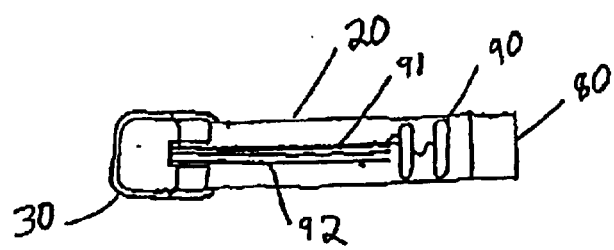
FIG. 17A is a top view.
Figure 17B:
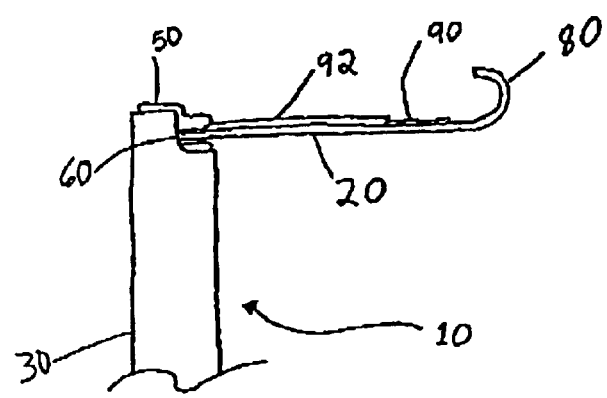
FIG. 17B is a side view of the distal end of the device of an embodiment of the invention. The probe includes an ablation unit, control wires, and a tube, mounted to the probe proximal of the distal tip. The anvil of the device has material removed in its central area to allow the retraction of the tube and control wires into the device.

The probe tip 80 may also be coupled to an ablation unit for ablating tissue, as shown in FIGS. 17A and 17B. The ablation unit can be attached to the probe member 20 preferably on the side facing the interior of the disc and proximal to the probe tip 80. In this configuration, the probe member 20 acts as a mechanical and thermal barrier minimizing unwanted ablation in the direction opposite the ablation unit, i.e. in the direction facing the interior aspect of the anulus. Ablation may be achieved using any of a variety of energy delivery techniques including, but not limited to light (laser), radio-frequency or electromagnetic radiation in either unipolar or bipolar configurations, resistive heating of the probe, ultrasound or the like.

An embodiment of a bipolar radio-frequency unit is depicted in FIG. 17. Power and control wires 91 may be deposited directly on to the probe member 20 as is known in the art. These wires act to connect RF elements 90 to an external power source and control unit affixed to or in communication with the advancer 40 and cannula 30. These elements 90 serve to allow the conduction of current therebetween, resulting in a resistive heating of the tissue in the region of the probe tip 80. These elements 90 are shown proximal to the distal probe tip 80 of device 10, but may be positioned at any location along probe 20 and/or on probe tip 80. Only two elements 90 are shown, however numerous elements may be positioned at various locations along the entire length of the probe 20 and be activated individually or multiplexed in pairs or groups to produce a desired temperature profile or ablation within the disc tissue.

Tube 92 is shown attached to probe 20 to provide an escape path for vapor and material ablated or for the infusion of fluids or gasses. These fluids or gasses may be added to alter the conductive characteristics of the tissue or may include various drugs, medications, genes or gene vectors or other materials to produce a desirable therapeutic affect. Tube 92 is shown with a single distal orifice. It may alternatively comprise any number of side holes or channels to increase the spread of fluids or gasses within the tissue or similarly to remove such materials as required by the procedure. Axial lumen are provided as needed to place the side holes or other apertures in communication with the proximal end of the device 10. The ablation unit could be activated as the probe member 20 is advanced through the tissues to create a cavity or activated as the probe member 20 is retracted after it has been advanced to a desired distance. Moreover, the power supplied to the ablation unit 90 could be varied according to the instantaneous velocity of the probe member 20 in order to ablate a more uniform cavity within the disc.

Whether used to dissect, resect or ablate tissue within the disc, device 10 may be used as part of an implantation procedure by creating a cavity or dissected region into which any of a variety of intradiscal implants or medications may be inserted. This region may be between or within anular layers 310, within the nucleus 320, or between the anulus 310 and nucleus 320. It may include a portion or the entirety of the nucleus. Increasing amounts of disc tissue may be removed by advancing and retracting the probe tip repeatedly at different depths within the disc. Intradiscal implants may be inserted independently using separate instrumentation or along, through, or around probe 20. Suitable implants include, among others, those disclosed in U.S. patent application Ser. No. 09/642,450 filed Aug. 18, 2000 entitled Devices and Methods of Vertebral Disc Augmentation, the disclosure of which is incorporated in its entirety herein by reference.

Figure 8:
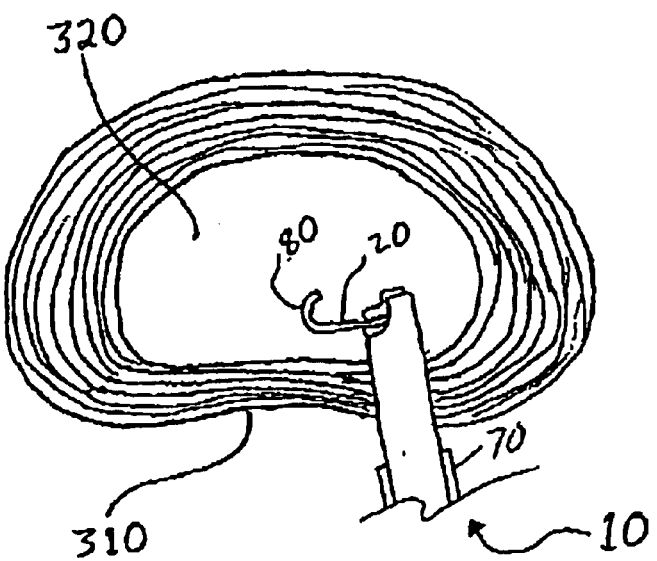
FIG. 8 depicts the probe of the device advanced relative to its starting position in FIG. 7 above.

FIGS. 7, 8, 9, and 10 depict an embodiment of the device 10 placed within an anulotomy or defect of anulus 300, which can be used to measure the thickness of anulus 310. In FIG. 7, the distal portion of the cannula 30 defined by the intradiscal tip 50 is inserted through the anulotomy or defect 300 to a depth wherein the probe 20 is inserted just beyond the anterior border of the posterior anulus 310. In FIG. 8, the probe member 20 is advanced out of cannula 30 and deflected by the deflection surface in curved passage 60 of the intradiscal tip 50 at an angle nearly perpendicular to device 10, causing the probe member 20 to advance parallel to the inner surface of the posterior anulus 310. In this use, the probe 20 need only be advanced outward several millimeters.

Figure 9:
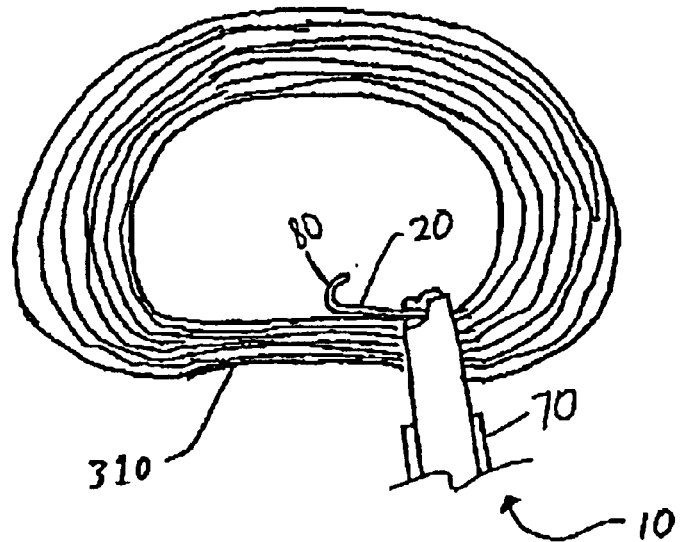
FIG. 9 depicts the intradiscal tip of the device with the probe resting on the inner surface of the posterior anulus.
Figure 10:
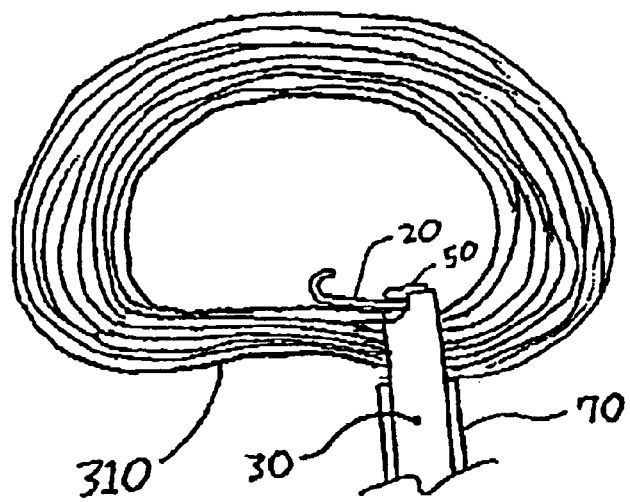
FIG. 10 depicts the device with the depth stop advanced to the posterior surface of the posterior anulus.

In FIG. 9, device 10 is proximally retracted from the anulotomy 300 until the probe 20 contacts the posterior anulus 310. In FIG. 10, a slideably adjustable depth stop 70 is carried by the cannula 30 and advanced distally (anteriorly) until it contacts the exterior surface of the posterior anulus 310 and the probe member 20 is in contact with the interior surface of the posterior anulus 310. The depth stop 70 functions by abutting anular tissue or surfaces of the vertebral body adjacent to the anulotomy 300 which impede further entry of the cannula 30 into the disc, such as may be determined by tactile feedback or under fluoroscopic visualization. FIG. 4 shows the depth stop adjustment knob 105, calibrated measurement marks 100 and depth stop 70. The cannula 30 or depth stop 70 may be marked with calibrated measurements 100 so that the distance between the intradiscal tip 50 at the point where the probe member 20 exits and the depth stop 70, can be determined. This distance corresponds to the thickness of the anulus adjacent to the anulotomy 300.

Figure 18:
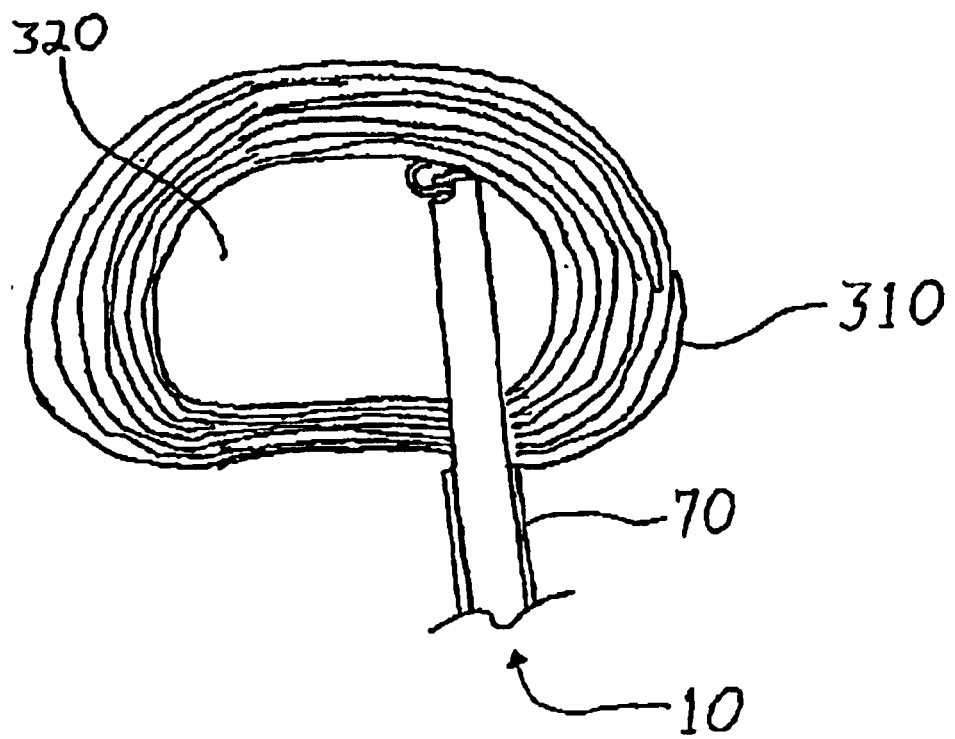
FIG. 18 is a transverse view of the intervertebral disc wherein the device is being used to measure the anterior to posterior distance from the anulotomy to the inner aspect of the anterior anulus.

FIG. 18 depicts an embodiment of the device 10 placed within an anulotomy or defect in anulus 300 and being used to determine the anterior-posterior dimension of the nuclear space as defined by the distance between the inner surfaces of the posterior anulus and the anterior anulus. Here, the probe member 20 and the adjustable depth stop 70 are fully retracted. The probe 20 and advancer 40 may be eliminated entirely in an embodiment intended solely for the anterior-posterior measurement described herein. The intradiscal tip 50 of the device 10 is advanced through the anulotomy or defect in anulus 300 until the inner surface of the anterior anulus is reached and impedes further travel of the intradiscal tip 50. In this manner the device 10 is used to provide tactile feedback of the disc's internal geometry. The adjustable depth stop 70 is then advanced distally toward the proximal exterior surface of the anulus or vertebral body and reading of the maximum depth reached can be obtained via calibrations on the proximal end of the device such as on the cannula. Electronic or other means could also be employed to measure and display this distance. The posterior anular thickness value can be subtracted from this to yield the distance between the inner aspects of the posterior and anterior anulus.

Figure 19:
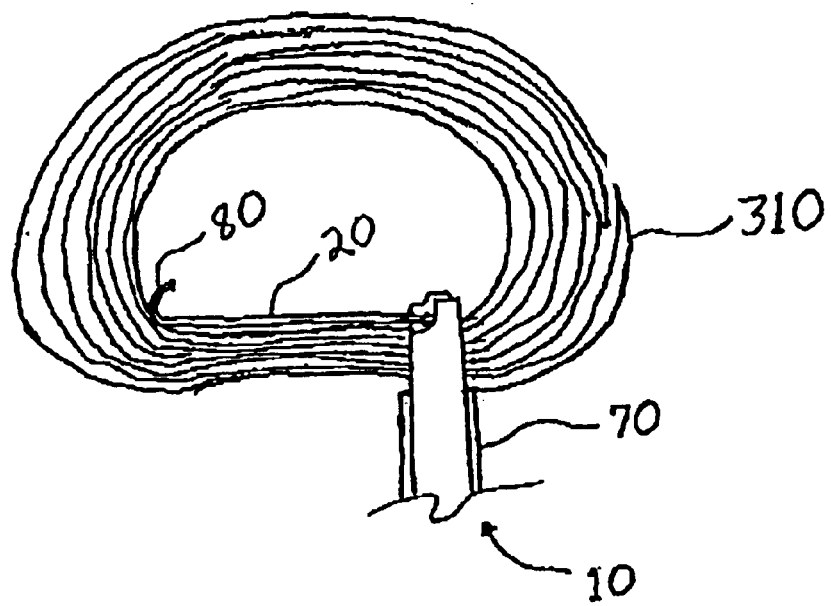
FIG. 19 is a transverse view of the intervertebral disc wherein the probe is advanced from the anulotomy to the far lateral corner.
Figure 20:
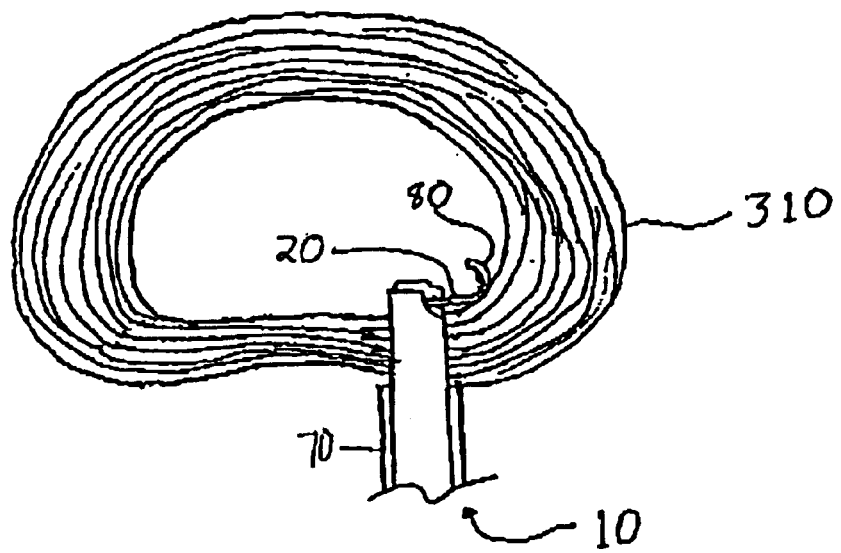
FIG. 20 is a transverse view of the intervertebral disc wherein the probe is advanced from the anulotomy to the near lateral corner.

FIGS. 19 and 20 depict an embodiment of the device 10 placed within an anulotomy or defect in anulus 300 and being used to determine the distance between the left and right lateral interior surfaces of the anulus. In measuring the distance between the left and right lateral surfaces of the anulus 310 the intradiscal tip 50 is inserted just beyond the interior wall of the posterior anulus, the probe tip 80 is advanced out of the curved passage 60 in the plane of the disc, i.e. parallel to the endplates, until tactile feedback from the advancer 40, indicates that lateral surface is resisting further advancement. Calibrated makings on the advancer 40 visible through or proximal to the cannula can then be used to determine this distance.

By rotating the device 10, while the probe member 20 is fully retracted, 180 degrees and performing the same action in the lateral direction, as shown in FIG. 20, one can obtain the total distance between the interior lateral surfaces. This method may be repeated at various depths within the disc by adjusting the depth stop 70. A similar method of using the probe member 20 to tactically interrogate the interior of the disc may be employed to dimension the distance between the vertebral endplates and relative distances from the anulotomy 300 to the endplates. All of the foregoing measurements may be taken either using a scoop shaped distal tip as shown, or a blunt, atraumatic tip without a scoop to minimize disruption of the nucleus.

Depth stop 70 may also be used to coordinate the dissection or resection of a space within the disc with the placement of another intradiscal instrument or implant. This method may be particularly useful for placing an implant along an inner surface of the anulus fibrosus. The thickness of the anulus as determined by any of the measurement techniques described above may be used for setting depth stops on other implantation instruments used to place an implant along the anulus. As an example, if the posterior anulus is measured to be 7 mm thick using device 10, a depth stop may be set on an implantation instrument to limit the penetration of this instrument into the disc to 7 mm or another depth that is relative to 7 mm. This would allow for an implant placed by this instrument to be inserted into a space previously dissected within the disc by device 10 along the inner surface of the posterior anulus.

Probe 20 may be used as part of the placement of an intradiscal implant in any of a variety of ways. One advantageous use of the probe 20 can be achieved by detaching it from advancer 40 once probe 20 is in a desired position within the disc space. Implants may then be passed along, behind or in front of probe 20 into this desired position. Probe 20 may then be removed from the disc space.

The measurement techniques described above may also be used to achieve the complete resection of the nucleus from the disc space. For example, a resection or ablation tip as described above may be passed repeatedly into the disc to the lateral borders of the nucleus. This process may be repeated at varying depths within the disc from the inner aspect of the posterior anulus to the inner aspect of the anterior anulus as determined by the depth stop.

While this invention has been particularly shown and described with references to preferred embodiments thereof, it will be understood by those skilled in the art that various changes in form and details may be made therein without departing from the scope of the invention encompassed by the appended claims.

What is claimed is:

1. A device comprising:
   a hollow delivery cannula having a distal end and a proximal end, said cannula dimensioned to fit within an iatrogenic hole or naturally occurring lesion in an anulus fibrosus;
   an advancer coupled to a probe member housed within said cannula, said probe member having a proximal end connected to said advancer and distal end connected to a probe tip, said probe member capable of being advanced outward from said distal end of said cannula; and
   a curved passage within said distal end of said cannula wherein said probe member travels through said passage and may be advanced outward therefrom at an angle between 30 and 150 degrees with respect to the longitudinal axis of the cannula and wherein the passage restricts travel of the probe with respect to the axis of the cannula substantially perpendicular to the longitudinal axis thereby preventing rotation of the probe.

2. The device of claim 1, further comprising:
   a means for measuring the distance advanced by the probe, said means coupled to said advancer; and
   a means for measuring the distance advanced by the cannula within said anulotomy or said lesion coupled to said cannula.

3. The device of claim 1, wherein the probe member has a noncircular cross-sectional geometry.

4. The device of claim 1, wherein the probe member has an ablation element coupled to said probe member proximal to said tip.

5. The device of claim 1, wherein the probe member comprises nitinol.

6. The device of claim 1, wherein the tip is selected from the group consisting of: a blunt-shaped tip, a sharpened tip, a scoop-shaped tip, and a chisel-shaped tip.

7. The device of claim 1, wherein the tip is curved backward facing towards the interior of the disc.

8. The device of claim 1, wherein the probe tip is curved downward with respect to the longitudinal axis and curved around until it faces the insertion device such that an interior aspect of the intervertebral disc is exposed only to a curved surface as the probe is deployed.

9. A device for treating the spine, comprising:
   an elongate guide having a longitudinal axis;
   an axially movable actuator, carried by the guide;
   a probe, movable with the actuator; and
   a deflection surface carried by the guide;
   a passage adjacent the deflection surface;
   wherein axial movement of the actuator causes the probe to advance along the deflection surface and through the passage at an angle relative to the longitudinal axis and wherein the passage restricts movement of the probe substantially perpendicular to the longitudinal axis there by preventing rotation of the probe.

10. A device for treating the spine as in claim 9, wherein the guide comprises an elongate tubular body having at least one lumen extending therethrough.

11. A device for treating the spine as in claim 10, wherein the actuator extends through at least a portion of the guide.

12. A device for treating the spine as in claim 9, wherein the probe comprises and elongate, flexible body attached to the actuator.

13. A device for treating the spine as in claim 12, wherein the probe is biased in a nonlinear configuration.

14. A device for treating the spine as in claim 13, wherein the probe comprises a nickel titanium alloy.

* * * * *

UNITED STATES PATENT AND TRADEMARK OFFICE
CERTIFICATE OF CORRECTION

PATENT NO. : 6,821,276 B2
APPLICATION NO. : 10/020507
DATED : November 23, 2004
INVENTOR(S) : Gregory H. Lambrecht et al.

Page 1 of 1

It is certified that error appears in the above-identified patent and that said Letters Patent is hereby corrected as shown below:

Title page Col. 2 item [74] (Attorney, Agent or Firm), line 2 after "Esq." insert -- ; Intrinsic Therapeutics, Inc. --.

Column 14, line 58 in claim 12, after "comprises" delete "and" and insert -- an --, therefor.

Signed and Sealed this

Twenty-second Day of July, 2008

JON W. DUDAS
*Director of the United States Patent and Trademark Office*